United States Patent [19]

Imamura

[11] 4,228,146
[45] Oct. 14, 1980

[54] METHOD OF PRODUCING RADIOACTIVE CARBON POWDER

[76] Inventor: Yuzo Imamura, No. 558 Junicho, Ibusuki, Kagoshima, Japan

[21] Appl. No.: 955,164

[22] Filed: Oct. 27, 1978

Related U.S. Application Data

[63] Continuation-in-part of Ser. No. 846,501, Oct. 27, 1977, abandoned.

[51] Int. Cl.² .............................................. A61K 43/00
[52] U.S. Cl. ......................................................... 424/1
[58] Field of Search ............................................. 424/1

[56] References Cited

PUBLICATIONS

Comprehensive Inorganic Chemistry, Bailar, Jr. et al., Ed., vol. I, Pergamon Press, Ltd., Oxford, England, 1973, pp. 193 and 328 to 330.
Shober, J. Am. Med. Assn., vol. 53, 1909, pp. 624 to 628.
Gübeli et al., Chem. Abs., vol. 49, pp. 4364 to 4365, (1955).
Failla, Archives of Radiology and Electrotherapy, Jun. 1920, pp. 1 to 17.

Primary Examiner—Leland A. Sebastian
Attorney, Agent, or Firm—Browdy and Neimark

[57] ABSTRACT

Carbon powder, placed in a hermetically closed apparatus under vacuum together with radium ore, adsorbs radon gas emanating from the radium ore thus producing a radioactive carbonaceous material, the radioactivity of which is due to the presence of adsorbed radon. The radioactive carbon powder thus obtained has excellent therapeutical efficacy and is suitable for a variety of applications because of the mild radioactivity of radon. Radium ore permits substantially limitlessly repeated production of the radioactive carbon powder.

1 Claim, 4 Drawing Figures

METHOD OF PRODUCING RADIOACTIVE CARBON POWDER

CROSS REFERENCE TO RELATED APPLICATION

This is a Continuation-in-Part of copending application Ser. No. 846,501, filed Oct. 27, 1977, now abandoned, the contents of which are incorporated by reference.

FIELD OF THE INVENTION

This invention relates to a method of producing radioactive carbon powder suitable for therapeutical use.

BACKGROUND OF THE INVENTION

Carbon powder has been a useful medical material. The medical value of carbon powder depends on its high capability of adsorbing bacteria, serum, lymph, filth, and other kinds of substances excreted from wounded skin or tissue cells.

On the other hand, radon therapy has been applied to medical treatment of rheumatism, neuritis, hypertension, inflammation of blood vessel, angina pectoris, maladjustment of blood vessels and sequelae of paralyses. It is described in the literature that allergic diseases, skin diseases, geriatric diseases, chronic inflammations, climacteric disorders, arrested growth of genitals, and infantile paralysis can also be effectively treated by radon therapy. These effects of radon therapy are considered due to the moderate radioactivity of radon.

Radon is a rare gas which emanates from radium ore when it decays by radiation. Radon is soluble in water and has only a transient existence with its radioactivity of a half-life less than 4 days. This imparts to the radon, which has an affinity to lipoids, a mild therapeutical efficacy. On the other hand, radium is a heavy metal and has radioactivity of extremely long half-life. If taken into the human body, it will stay there and effect an undesirable overexposure to the body.

The biochemical actions of radon on the human body are as follows:

(1) anti-anaphylaxis effects,
(2) action on the endocrine system,
(3) action on the nerve center or on the hypophysis-adrenal system, affecting the purine metabolism,
(4) action on the circulatory system; particularly improvement of blood delivery of the heart, and a good effect on the hypertensive patient,
(5) action on the nerve system which has affinity to radon, thus softening pain, and
(6) action on the digestive organs, particularly on the empty stomach, animating the peristaltic motion of the stomach for a comparatively long time.

In therapeutical use, radon is usually isolated and filled into previously evacuated gold or glass capillary tubes, thus forming so-called "random tubes" or "seeds", which are applied to the situs of disease where alpha-rays from the radon will reach such situs. In some cases, the tubes may be previously filled with active carbon, on which the isolated radon is adsorbed.

Because radon is strongly adsorbed on solid radium surfaces, its isolation process is carried out usually in aqueous solution. This process, however, is very complicated and greatly increases the costs of radon tube preparation, thus making radon therapy very expensive in conjunction with the comparatively short half-life of radon, as mentioned above.

No idea has been proposed for therapeutical purposes to use carbon powder that is saturated with radon gas by directly exposing the carbon powder to radioactive radium ore.

SUMMARY OF THE INVENTION

According to the present invention, there is provided a method of preparing carbon powder with radon gas adsorbed therein and capable of radiating alpha-rays, which powder can be used as a fundamental raw material in preparing medicines. The method comprises placing carbon powder in a hermetically closed apparatus under a vacuum together with radium ore or sinter deposits that contain radium, and allowing the carbon powder to absorb the radon gas emanating from the radium ore during the radiation process.

BRIEF DESCRIPTION OF THE DRAWINGS

The objects and advantages of the present invention will appear more fully from the following description referring to the accompanying drawings, in which.

DETAILED DESCRIPTION OF EMBODIMENT

Figure 1:
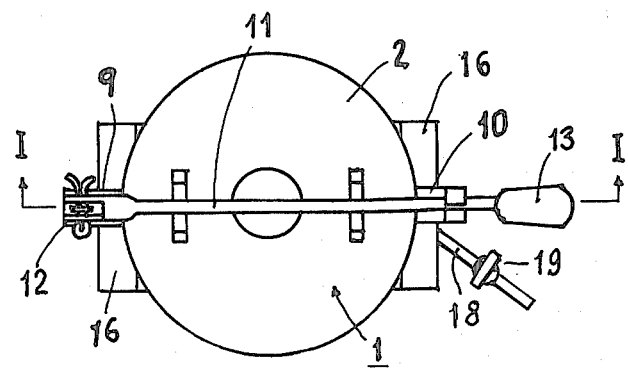
FIG. 1 is a plan view of an apparatus as used in the process of the invention.
Figure 2:
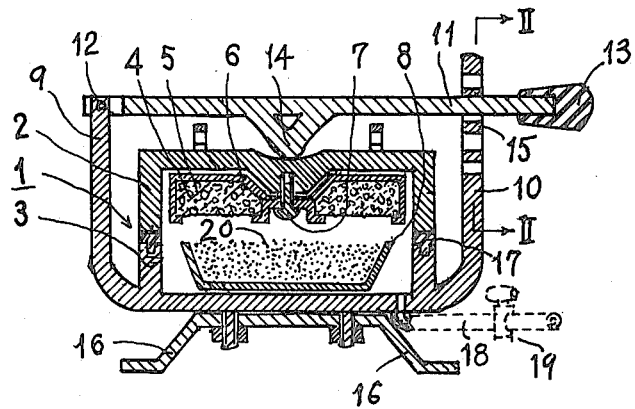
FIG. 2 is a sectional elevation along the line I—I of the apparatus shown in FIG. 1.
Figure 3:
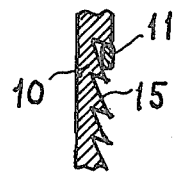
FIG. 3 is a partial sectional view along the line II—II in FIG. 2.

Referring now to FIGS. 1 and 2, a radiation box 1 is composed of a lid 2 and a receptacle 3. Grains of radium ore 4 contained in a bonding agent 5 are held in a pan 6 fixed to the inside of the lid 2 with a bolt 7. A dish 8 is set in the receptacle 3, the open dish 8 facing the radium ore 4.

The receptacle 3 has arms 9, 10, both extending upwardly from the bottom thereof. A pressing bar 11 is connected to the arm 9 with a hinge 12 on one end, and is attached with handle 13 on the other end. In the middle portion of the bar 11, a protrusion 14 projects downwardly therefrom. A saw-toothed locking mechanism 15 for the pressing bar 11 is provided on the arm 10. Legs 16 are attached to the bottom of the radiation box to support the apparatus.

A rubber packing 17 is interposed between the lid 2 and the receptacle 3 to make the radiation box airtight. On the bottom of the receptacle 3, there is provided an outlet pipe 18 with a cock 19, at which air is extracted from the radiation box 1 by means of a vacuum pump (not shown).

Now, the process of the invention will be described in detail.

An amount of carbon powder 20 is put into the dish 8 and preheated to some extent. Then the dish 8 with the carbon powder is set in the receptacle 3 as shown in FIG. 1 before the powder is cooled. After an amount of water is sprayed on the radium ore grains 4, the lid 2 is fitted to the receptacle. The bar 11 is pressed down to press the lid 2 by means of its protrusion 14 to make the radiation box 1 airtight by virtue of the packing 17, and fixed to the lowest possible position of the saw-tooth locking device 15.

Then the vacuum pump connected to the outlet pipe 18 is operated to extract air from the radiation box.

When the vacuum inside the radiation box has reached the desired degree, the cock 19 is closed and the pump is stopped.

The rate at which the radon is adsorbed by the carbon powder is usually lower at first and gradually increases. After 6 to 8 hours from the start of treatment, it reaches the highest level and then gradually drops until the carbon powder is saturated.

Any radium ore that has a certain degree of radium content can be used as the radon source of the present method. In the example given below, radioactive sinter deposits recently found in a hot spring at the southwest foot of Mt. Takakuma in Southern Kyushu, Japan, were used. The radium concentration in some of the deposits has proved highest ever reported in the world.

There is substantially no difference between boneblack and active carbon made from palm coconuts as the carbon powder to be used in the present method.

Remarkable advantages of the radioactive carbon powder prepared according to the method of the invention are:

(1) Adequate radioactivity for therapeutical uses which continues for several days.

(2) Easy preparation of medicines for external usage, such as ointments, unguents and fomentations.

(3) Versatile utility such as direct application in the form of ointment, unguent, salve or fomentation to skin injuries such as cuts after operations.

(4) Equivalent effect by oral dosage to that of conventional radon remedy such as "cave remedy" and "inhalation remedy".

It is particularly pointed out that the radium material permits almost limitlessly repeated use for the production of the radioactive carbon powder.

The following example is offered illustratively:

EXAMPLE

Radioactive sinter deposits from the hot spring at the southwest foot of Mt. Takakuma was filled in the pan 6 and fixed to the lid 2 as shown in FIG. 2. This material showed 25,000 CPM (count per minute) of radiation by survey meter. Five hundred grams of boneblack was put into the dish 8 and, after being lightly preheated, placed in the receptacle 3. The sinter deposits were sprayed with water, and the radiation box was closed and evacuated by means of a vacuum pump to about 10 mm Hg, according to the procedure described above.

Figure 4:
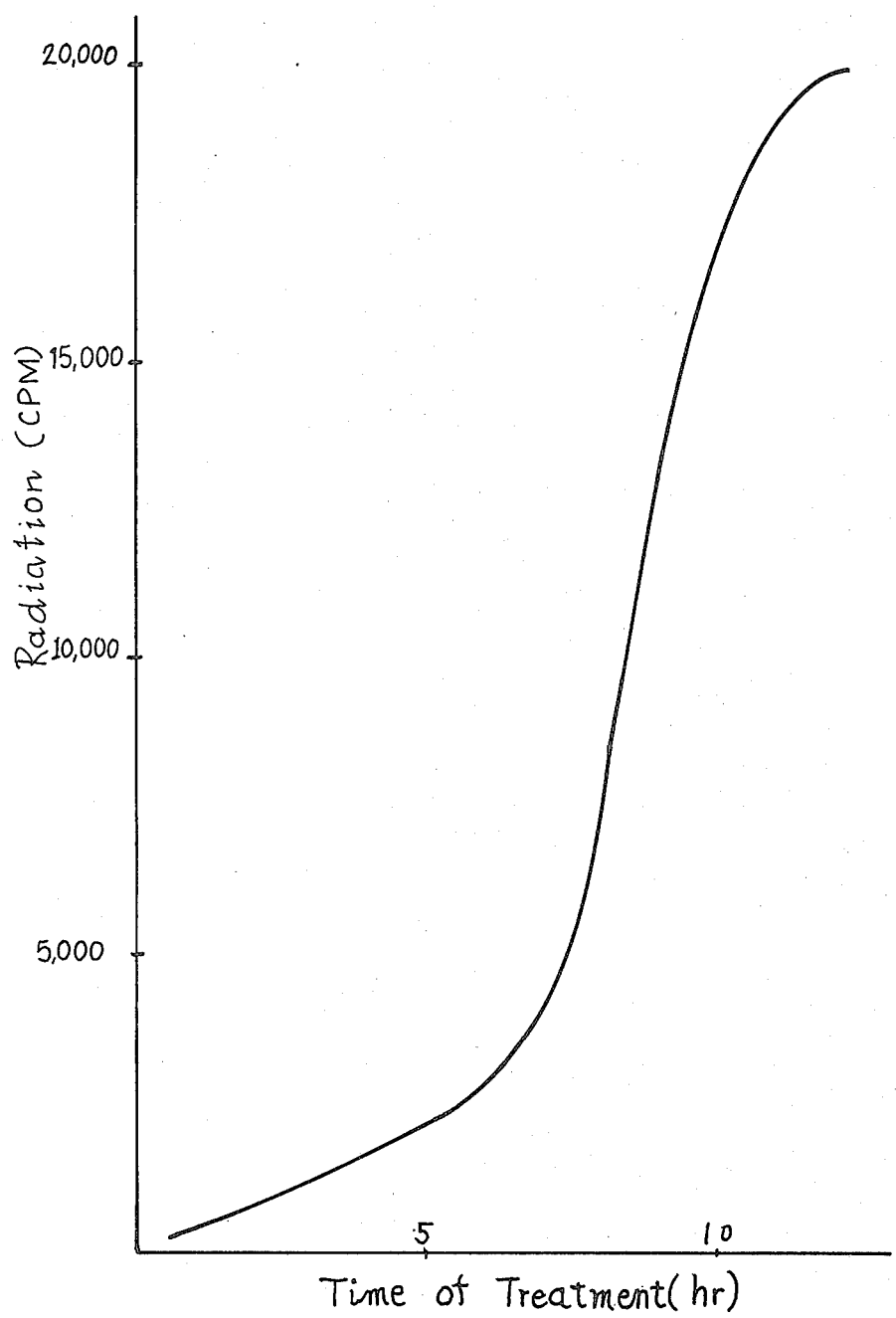
FIG. 4 is a graph showing the change in radioactivity of boneblack during treatment.

The change in radioactivity of the boneblack was measured by means of the survey meter every hour from the beginning. The results are shown in Table 1 and FIG. 4.

TABLE 1

| Time of treatment (hours) | Radiation (CPM) | Time of treatment (hour) | Radiation (CPM) |
|---|---|---|---|
| 1 | 500 | 7 | 4,000 |
| 2 | 700 | 8 | 8,000 |
| 3 | 1,500 | 9 | 12,000 |
| 4 | 1,500 | 10 | 16,000 |
| 5 | 2,000 | 11 | 20,000 |
| 6 | 2,500 | 12 | 20,000 |

After being saturated, the sample boneblack was taken out of the apparatus and the count of radiation was measured every day to show the degradation of its radioactivity. This is shown in Table 2.

TABLE 2

| Lapsed time (day) | Radiation (CPM) |
|---|---|
| 2 | 12,000 |
| 3 | 8,000 |
| 4 | 4,000 |
| 5 | 2,000 |
| 6 | 1,000 |
| 7 | 1,000 |

The therapeutical effect depends upon the count of radiation of the treated carbon powder relative to the position and condition of the focus. For pain, for example, the higher the count value, the better. Direct contact of the carbon powder to the situs of disease for about 20 to 50 minutes mitigates the pain, and repeated application in 2 or 3 days removes the pain. When used as an ointment, on the other hand, radon containing carbon powder of low count is suitable (e.g. that after 4 days from the treatment) since it is applied for relatively long time.

It will be obvious to those skilled in the art that various changes may be made without departing from the scope of the invention and the invention is not to be considered limited to what is shown in the drawings and described in the specification.

What is claimed is:

1. A method for the production of radioactive carbon powder with radon gas absorbed therein and capable of radiating alpha-rays using an apparatus comprising a receptacle with a removable lid capable of being closed in an airtight fashion and with means to extract air from the receptacle, comprising:
   affixing grains of radium ore contained in a bonding agent to the inside of the lid;
   placing preheated carbon powder into the receptacle;
   spraying water on the radium grains;
   pressing the lid against the receptacle, before the powder is cooled, to make the receptacle airtight; and
   extracting air from the airtight receptacle.

* * * * *